(12) United States Patent
Boldig et al.

(10) Patent No.: US 10,118,334 B2
(45) Date of Patent: Nov. 6, 2018

(54) WIRE-REINFORCED TUBING AND METHOD OF MAKING THE SAME

(71) Applicant: Custom Wire Technologies, Inc., Port Washington, WI (US)

(72) Inventors: Robert Boldig, Port Washington, WI (US); Michael Boldig, Port Washington, WI (US); James Boldig, Belgium, WI (US); Zachary Judy, Columbus, OH (US)

(73) Assignee: Custom Wire Technologies, Inc., Port Washington, WI (US)

( * ) Notice: Subject to any disclaimer, the term of this patent is extended or adjusted under 35 U.S.C. 154(b) by 377 days.

(21) Appl. No.: 15/210,069

(22) Filed: Jul. 14, 2016

(65) Prior Publication Data

US 2018/0015658 A1    Jan. 18, 2018

(51) Int. Cl.
| | |
|---|---|
| *B32B 37/00* | (2006.01) |
| *B29C 63/24* | (2006.01) |
| *B29C 47/00* | (2006.01) |
| *A61L 29/04* | (2006.01) |
| *A61M 25/00* | (2006.01) |
| *B29C 41/00* | (2006.01) |

(Continued)

(52) U.S. Cl.
CPC .............. *B29C 63/24* (2013.01); *A61L 29/04* (2013.01); *A61M 25/00* (2013.01); *B29C 41/00* (2013.01); *B29C 41/085* (2013.01); *B29C 41/20* (2013.01); *B29C 47/0023* (2013.01); *B29C 47/0066* (2013.01); *B29C 69/02* (2013.01); *B29C 47/021* (2013.01); *B29C 63/0004* (2013.01); *B29K 2021/003* (2013.01); *B29K 2023/06* (2013.01); *B29K 2675/00* (2013.01); *B29L 2023/007* (2013.01); *B29L 2031/7542* (2013.01)

(58) Field of Classification Search
CPC ....... B29C 63/24; B29C 41/00; B29C 41/085; B29C 41/20; B29C 47/0023; B29C 47/0066; B29C 69/02; A61L 29/04; B61M 25/00
USPC ........................................................ 156/73.5
See application file for complete search history.

(56) References Cited

U.S. PATENT DOCUMENTS

| | | |
|---|---|---|
| 4,776,844 A | 10/1988 | Ueda |
| 4,900,314 A | 2/1990 | Quackenbush |

(Continued)

FOREIGN PATENT DOCUMENTS

| | | |
|---|---|---|
| JP | 6254164 | 9/1994 |
| JP | 2008253297 | 10/2008 |

OTHER PUBLICATIONS

International Search Report dated Jul. 18, 2017.

*Primary Examiner* — James D Sells
(74) *Attorney, Agent, or Firm* — Reinhart Boerner Van Deuren, s.c.

(57) ABSTRACT

An apparatus for and method of manufacturing an improved wire-reinforced plastic tubing for medical and other applications is disclosed. A plurality of spaced-apart wire segments may be wound onto successive portions of a long segment of plastic tubing which portions are supported for rotation to wind coil wire thereon by rotating the plastic tubing while a supply of coil wire is wound onto the plastic tubing. When multiple winding segments have been wound on the long segment of plastic tubing, the segments may be separated into individual wire-reinforced tubing products each having one or more wire windings thereupon.

20 Claims, 7 Drawing Sheets

(51) Int. Cl.
  *B29C 69/02* (2006.01)
  *B29C 41/08* (2006.01)
  *B29C 41/20* (2006.01)
  *B29C 63/00* (2006.01)
  *B29C 47/02* (2006.01)
  *B29K 675/00* (2006.01)
  *B29L 23/00* (2006.01)
  *B29K 21/00* (2006.01)
  *B29L 31/00* (2006.01)

(56) References Cited

U.S. PATENT DOCUMENTS

| | | |
|---|---|---|
| 5,069,382 A | 12/1991 | Misiak et al. |
| 5,630,806 A | 5/1997 | Inagaki et al. |
| 5,637,168 A | 6/1997 | Carlson |
| 5,741,452 A | 4/1998 | Ryan et al. |
| 5,906,036 A | 5/1999 | Pagan |
| 6,130,406 A | 10/2000 | Cheer |
| 6,206,824 B1 | 3/2001 | Ohara et al. |
| 6,554,820 B1 | 4/2003 | Wendlandt et al. |
| 6,669,886 B1 | 12/2003 | Willard |
| 6,849,085 B2 | 2/2005 | Marton |
| 7,582,079 B2 | 9/2009 | Wendlandt et al. |
| 7,905,877 B1 * | 3/2011 | Jimenez .......... A61M 25/0012 604/523 |
| 8,066,926 B2 | 11/2011 | Fogarty |
| 8,529,719 B2 * | 9/2013 | Pingleton .......... A61M 25/0009 156/169 |
| 8,622,994 B2 | 1/2014 | Wendlandt et al. |
| 9,504,476 B2 * | 11/2016 | Gulachenski ...... A61B 17/1214 |
| 2005/0131387 A1 | 6/2005 | Pursley |
| 2005/0165366 A1 | 7/2005 | Brustad et al. |
| 2007/0095042 A1 | 5/2007 | Bieszczad et al. |
| 2007/0096357 A1 | 5/2007 | Yamada et al. |
| 2007/0215268 A1 | 9/2007 | Piingleton et al. |
| 2009/0012500 A1 | 1/2009 | Murata et al. |
| 2009/0236770 A1 | 9/2009 | Fogarty |
| 2009/0240235 A1 | 9/2009 | Murata |
| 2009/0299333 A1 | 12/2009 | Wendlandt et al. |
| 2010/0057052 A1 | 3/2010 | Tsukumo et al. |
| 2011/0005661 A1 | 1/2011 | Brustad et al. |
| 2011/0190732 A1 | 6/2011 | Majercak et al. |
| 2011/0190664 A1 | 8/2011 | Majercak et al. |
| 2011/0245807 A1 | 10/2011 | Sakata et al. |
| 2013/0327469 A1 | 12/2013 | Pingleton et al. |

* cited by examiner

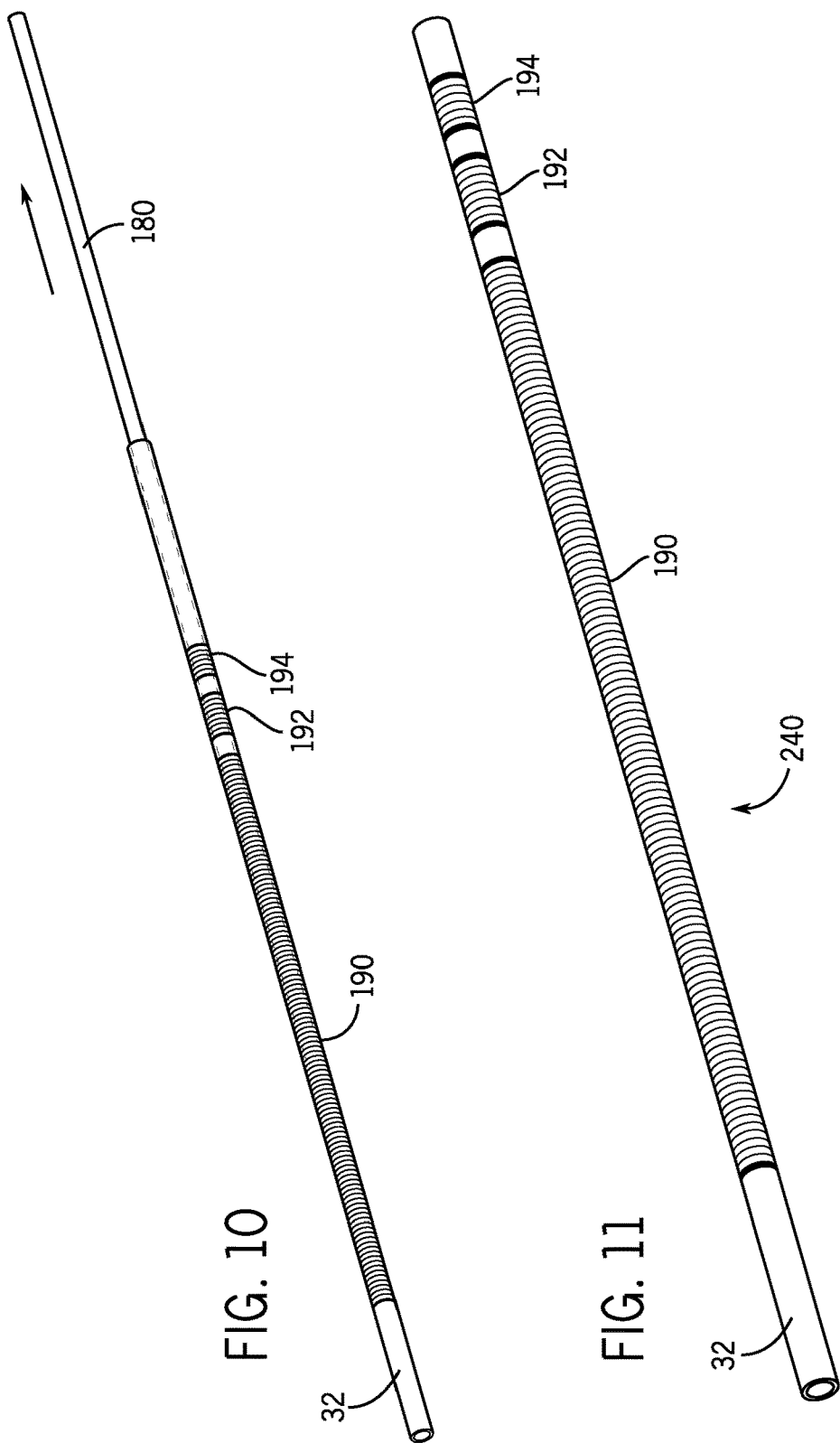

WIRE-REINFORCED TUBING AND METHOD OF MAKING THE SAME

BACKGROUND OF THE INVENTION

Field of the Invention

The present invention relates generally to wire-reinforced plastic tubing, and more particularly to an improved wire-reinforced plastic tubing segment for medical and other applications and an apparatus for and a method of making the same in a relatively less expensive large scale manner.

Lengths of plastic tubing are used extensively in medical and other applications for routing fluids from one location to another. Such plastic tubing is relatively thin-walled, and thus is relatively flexible. One example of such a medical application is the tubing used for a heart-lung machine that is used during open heart surgery, in which blood is pumped through the segments of plastic tubing. In such medical applications, it is imperative that the tubing must not kink, since a kink could prevent the passage of fluid through the tubing with serious adverse consequences.

In such medical applications, the plastic tubing typically has a helically-wound wire support member placed on the outer surface of the tubing to prevent sudden bends from occurring in the tubing. At present, the helically-wound wire support member is first wound and is then subsequently placed onto a length of the tubing. To complete the manufacturing process, an outer plastic layer is installed over the helically-wound wire support member to retain it in place. This outer plastic layer may be extruded over the inner plastic tubing and the helically-wound wire support member located thereupon, or the outer plastic layer may be sprayed onto this assembly, or it may be applied by dipping the assembly into a liquid plastic material that subsequently hardens on it.

One alternative example of a method of manufacturing a wire-reinforced tubing may be found in U.S. Pat. No. 8,529,719, to Pingleton et al., which discloses a method of making medical tubing using thermal winding which winds a plastic coated wire around a mandrel while simultaneously heating the plastic coating to melt it to form a tube. Another alternative example of a method of manufacturing a wire-reinforced tubing may be found in U.S. Pat. No. 8,066,926 to Fogarty, which discloses a method of manufacturing reinforced medical tubing with an inner layer of tubing having an outer surface with a recessed pathway defined therein, with a metallic reinforcement member formed in the recessed pathway and an outer layer molded over the inner layer and the reinforcement member.

Still another alternative example of a method of manufacturing a wire-reinforced tubing may be found in U.S. Pat. Nos. 6,554,820, 7,582,079, and 8,622,994, all to Wendlandt et al., which disclose a method of manufacturing a medical tube having a braid and a helical flat metal coil in the tube. The coils and braid can be assembled on a cylindrical core, and then the assembly can be heated and dipped in molten plastic to coat the components, and then cured in an oven. Alternately, the braid and coil can be assembled, and tubular plastic layers including a heat shrink layer can be placed on the assembly, which is then heated, causing the plastic layers to melt and shrink onto the braid and coils.

These techniques are all either technically difficult or labor intensive to manufacture the wire reinforced tubing in this manner, or both. It is accordingly the primary objective of the present invention that it provide an improved wire-reinforced tubing and/or an improved process of manufacturing such a wire-reinforced tubing.

It will thus be appreciated that it would be desirable to provide an apparatus for and a method of manufacturing the wire-reinforced tubing product referenced above for medical and other applications.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

The disadvantages and limitations of the background art discussed above are overcome by the present invention. With this invention, a better apparatus for and method of manufacturing wire-reinforced tubing for medical and other applications is disclosed which may be used to produce a substantially improved wire-reinforced tubing product.

The present invention begins by providing an extended length of plastic tubing that optionally has a thicker walled segment of plastic support tubing located inside the plastic tubing to stiffen and support the thinner walled plastic tubing. The thicker walls of the plastic support tubing makes it substantially stiffer than the thinner-walled plastic tubing. The plastic tubing and the plastic support tubing may be made of an extruded multi-layered thermoplastic elastomer. In one embodiment, the plastic tubing and the plastic support tubing may be a common material such as polyurethane.

The plastic tubing/plastic support tubing may be manufactured in extended lengths and wound onto a supply reel. The wire winding process may be carried out on a machine having a mount for the supply reel, a pair of air-operated chucks, and a mount for a take-up reel, all of which are mounted for rotation together. The plastic tubing/plastic support tubing is fed from the supply reel through the two air-operated chucks, and then onto the take-up reel.

The wire winding operation is performed on the segment of the plastic tubing/plastic support tubing extending between the two air-operated chucks, which function to retain the segment of plastic tubing/plastic support tubing between the two air-operated chucks rigid during the winding operation. A first end of the wire is started to be wound onto the outer surface of the plastic tubing as the machine rotates the supply reel, the pair of air-operated chucks and the segment of the plastic tubing/plastic support tubing extending therebetween, and the mount for a take-up reel. The initial windings onto the plastic tubing are wound immediately adjacent each other, and a laser may be used to tack these windings together to retain them tightly on the plastic tubing. The laser may vaporize the portion of the first end of the wire extending from the winding.

The winding process continues, with the bulk of the windings being spaced further apart so that they are not immediately adjacent each other. At the end of the windings, the terminal windings on the plastic tubing are also wound immediately adjacent each other, and a laser may be used to tack these windings together to retain them tightly on the plastic tubing. The laser may then vaporize the portion of a second end of the wire extending from the winding. Alternatively, an appropriate adhesive may be used to retain the winding in place on the plastic tubing.

The air-operated chucks are then opened, and the segment of the plastic tubing/plastic support tubing extending between the two air-operated chucks, which now has the helically-wound wire support member thereupon, is moved toward the take-up reel. The air-operated chucks are then closed over the next segment of the plastic tubing/plastic support tubing, and the winding operation is repeated.

Once the extended length of the plastic tubing/plastic support tubing with multiple spaced-apart helically-wound wire support segments thereupon is complete, the extended length wire-reinforced plastic tubing/plastic support tubing may have an outer plastic surface made of a material such as polyethylene installed over the outer surface thereof. The outer plastic layer may be extruded over the plastic tubing/ plastic support tubing and the helically-wound wire support member, or it may be sprayed thereupon, or the segment may be dipped into liquid plastic.

Next, segments of the extended length plastic coated wire-reinforced plastic tubing/plastic support tubing may be cut to length, and, if used, the plastic support tubing may then be removed from the interior of the plastic tubing. This may be done by gripping both ends of the segment of the plastic support tubing, and stretching it to cause it to shrink in outer diameter, and then pulling it out of the interior of the plastic tubing.

In a manufacturing method embodiment, a method of manufacturing wire-reinforced plastic tubing segments includes: supplying an extended length segment of plastic tubing from a supply reel; supporting a portion of the plastic tubing supplied from the supply reel intermediate two spaced-apart air chucks, the portion of the plastic tubing located intermediate the air chucks defining an axis of rotation; taking up the plastic tubing onto a take-up reel; simultaneously rotating the supply reel, the air chucks, and the take-up reel about the axis of rotation while supplying a reinforcing wire to the portion of the plastic tubing located intermediate the air chucks to helically wind at least one wire winding onto the portion of the plastic tubing located intermediate the air chucks; releasing the air chucks and advancing the plastic tubing from the supply reel to the take-up reel to advance a subsequent portion of the plastic tubing to the location between the air chucks and supporting the subsequent portion of the plastic tubing with the air chucks; repeating the rotating and releasing steps; installing an outer plastic layer over the exterior of the plastic tubing and the wire windings thereupon; and cutting the plastic tubing into segments each having at least one wire winding.

In another manufacturing method embodiment, a method of manufacturing wire-reinforced plastic tubing segments includes: supplying an extended length segment of plastic tubing having an extended length segment of plastic support tubing located inside the extended length segment of plastic tubing from a supply reel; supporting a portion of the plastic tubing/plastic support tubing supplied from the supply reel intermediate two spaced-apart air chucks, the portion of the plastic tubing/plastic support tubing located intermediate the air chucks defining an axis of rotation; taking up the plastic tubing/plastic support tubing onto a take-up reel; simultaneously rotating the supply reel, the air chucks, and the take-up reel about the axis of rotation while supplying a reinforcing wire to the portion of the plastic tubing/plastic support tubing located intermediate the air chucks to helically wind at least one wire winding onto the portion of the plastic tubing/plastic support tubing located intermediate the air chucks; welding first and second opposite ends of the at least one wire winding that is helically wound onto the portion of the plastic tubing/plastic support tubing located intermediate the air chucks; releasing the air chucks and advancing the plastic tubing/plastic support tubing from the supply reel to the take-up reel to advance a subsequent portion of the plastic tubing/plastic support tubing to the location between the air chucks and supporting the subsequent portion of the plastic tubing/plastic support tubing with the air chucks; repeating the rotating, welding, and releasing steps; installing an outer plastic layer over the exterior of the plastic tubing and the wire windings thereupon; cutting the plastic tubing into segments each having at least one wire winding; and removing the plastic support tubing from the segments of plastic tubing.

In still another manufacturing method embodiment, a method of manufacturing wire-reinforced plastic tubing segments includes: providing an extended length segment of plastic tubing; supporting a portion of the plastic tubing intermediate two spaced-apart air chucks, the portion of the plastic tubing located intermediate the air chucks defining an axis of rotation; simultaneously rotating the air chucks about the axis of rotation while helically winding a wire winding onto the portion of the plastic tubing located intermediate the air chucks; releasing the air chucks and advancing the plastic tubing to provide a subsequent portion of the plastic tubing to the location between the air chucks and supporting the subsequent portion of the plastic tubing with the air chucks; repeating the rotating and releasing steps; installing an outer plastic layer over the exterior of the plastic tubing and the wire windings thereupon; and cutting the plastic tubing into segments each having at least one wire winding.

In a manufacturing apparatus embodiment, an apparatus for manufacturing wire-reinforced plastic tubing segments includes: a supply reel at one end of the apparatus that is arranged and configured to contain a supply of an extended length segment of plastic tubing; a take-up reel at an opposite end of the apparatus that is arranged and configured to take up the plastic tubing; two spaced-apart air chucks located on the apparatus intermediate the supply reel and the take-up reel, the air chucks supporting a portion of the plastic tubing supplied from the supply reel that is located intermediate the air chucks and that defines an axis of rotation; and a mechanism configured to supply a reinforcing wire to the portion of the plastic tubing located intermediate the air chucks while the supply reel, the air chucks, and the take-up reel are simultaneously rotated about the axis of rotation to helically wind at least one wire winding onto the portion of the plastic tubing located intermediate the air chucks; wherein the apparatus is arranged and configured to release the air chucks and advance the plastic tubing from the supply reel to the take-up reel to advance a subsequent portion of the plastic tubing to the location between the air chucks and support the subsequent portion of the plastic tubing with the air chucks, following which the rotating and releasing steps are repeated to helically wind additional wire windings onto the portion of the plastic tubing located intermediate the air chucks.

The wire-reinforced tubing manufacturing apparatus and method of the present invention may be used to produce an improved wire-reinforced tubing product. The wire-reinforced tubing product produced by the apparatus and method of the present invention is advantageous for use with medical and other applications. Finally, the wire-reinforced tubing apparatus and method of the present invention achieves numerous advantages without incurring any substantial relative disadvantage.

DESCRIPTION OF THE DRAWINGS

These and other advantages of the present invention are best understood with reference to the drawings, in which:

FIG. 10 is an isometric view of the segment of tubing with the three windings shown in FIG. 9 showing the optional support tubing being removed therefrom;

FIG. 11 is an isometric view of the segment of tubing with the three windings shown in FIG. 10 cut to its final length from continuous length of tubing.

DETAILED DESCRIPTION OF THE PREFERRED EMBODIMENT

Figure 1:
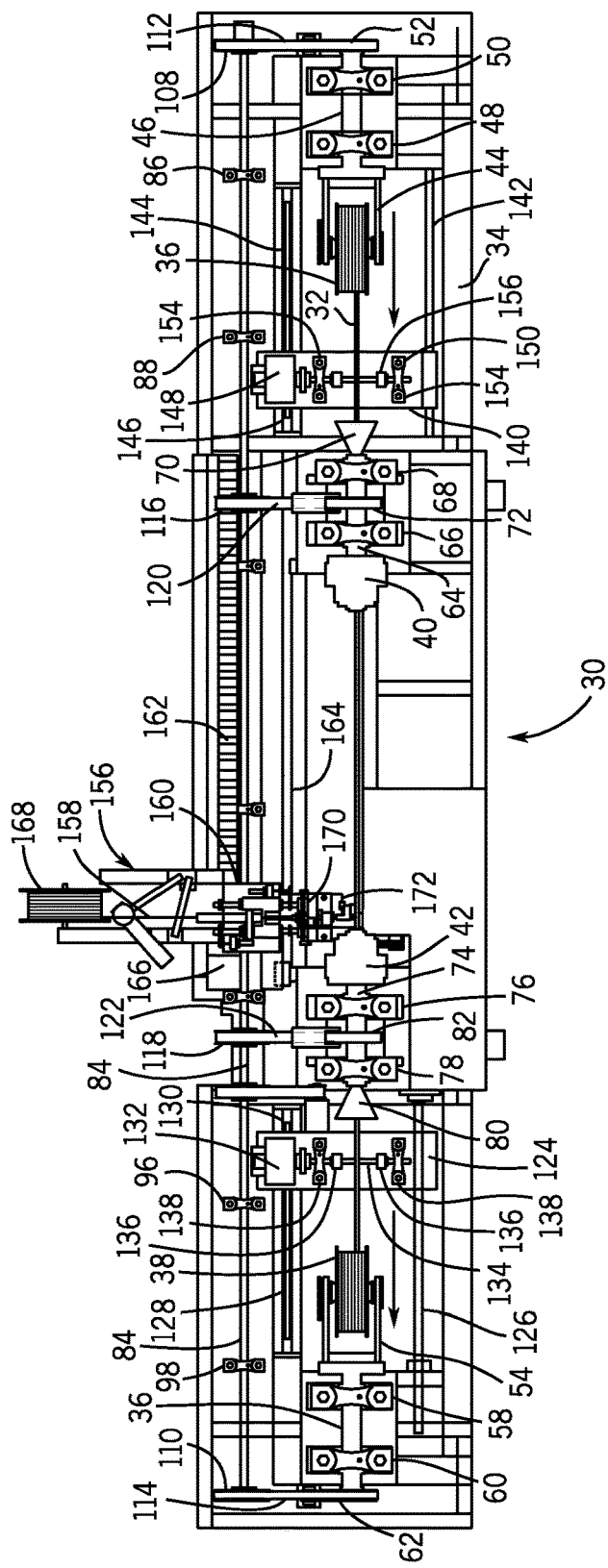
FIG. 1 is a top plan view of an apparatus for winding wire-reinforcement segments onto a continuous length of tubing.
Figure 2:
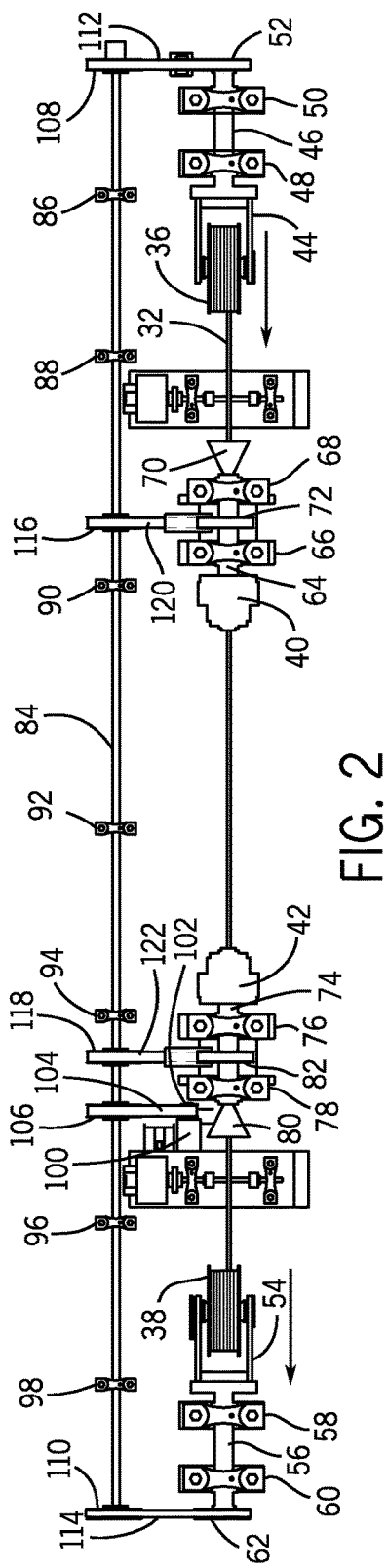
FIG. 2 is a top plan view of the components of the apparatus shown in FIG. 1 which rotate the tubing.

A preferred embodiment of an apparatus 30 for winding wire-reinforcement segments onto a continuous length of tubing is illustrated in FIG. 1, with the components of this apparatus 30 that are used to rotate the continuous length of tubing 32 being shown with all other components removed for clarity in FIG. 2. All of the components are mounted on a base, indicated generally by the reference numeral 34. The continuous length of tubing 32 is supplied from a supply reel 36 located near the left side of the apparatus 30 for winding wire-reinforcement segments in the view shown in FIG. 1 and it is collected onto a take-up reel 38 located near the right side of the apparatus 30 for winding wire-reinforcement segments in the view shown in FIG. 1.

The continuous length of tubing 32 thus extends between the supply reel 36 and the take-up reel 38, and passes through a first air chuck 40 located nearer to the supply reel 36 than it is to the take-up reel 38, and a second air chuck 42 located nearer to the take-up reel 38 than it is to the supply reel 36. The first air chuck 40 and the second air chuck 42 use air pressure to selectively either grip the portion of the continuous length of tubing 32 passing therethrough or release the continuous length of tubing 32 so that it can move axially freely therethrough. The air chucks 40 and 42 may be, for example, Atlas Workholding air-Powered front mount 5C dead length collet chucks or the like.

The supply reel 36 is rotatably mounted on a reel support bracket 44 attached to one end of a reel support shaft 46 that is mounted for rotation on a pair of bearing support assemblies 48 and 50 (which are supported from the base 34). A reel drive pulley 52 is attached at the other end of the reel support shaft 46. Similarly, the take-up reel 38 is rotatably mounted on a reel support bracket 54 attached to one end of a reel support shaft 56 that is mounted for rotation on a pair of bearing support assemblies 58 and 60 (which are supported from the base 34). A reel drive pulley 62 is attached at the other end of the reel support shaft 46.

The first air chuck 40 is rotatably mounted on a hollow air chuck support shaft 64 that is mounted for rotation on a pair of bearing support assemblies 66 and 68 (which are supported from the base 34). A hollow guide cone 70 is attached at the other end of the hollow air chuck support shaft 64. An air chuck drive pulley 72 is mounted on the hollow air chuck support shaft 64 intermediate the bearing support assembly 66 and 68. It will be appreciated that the continuous length of tubing 32 thus extends from the supply reel 36 and consecutively through the hollow guide cone 70, the hollow air chuck support shaft 64, and the first air chuck 40, and then to the second air chuck 42.

The second air chuck 42 is rotatably mounted on a hollow air chuck support shaft 74 that is mounted for rotation on a pair of bearing support assemblies 76 and 78 (which are supported from the base 34). A hollow guide cone 80 is attached at the other end of the hollow air chuck support shaft 74. An air chuck drive pulley 82 is mounted on the hollow air chuck support shaft 74 intermediate the bearing support assembly 76 and 78. It will be appreciated that the continuous length of tubing 32 thus extends from the first air chuck 40 and consecutively through the second air chuck 42, the hollow air chuck support shaft 74, and the hollow guide cone 80, and then to the take-up reel 38.

It should be noted that the reel support shaft 46, the hollow air chuck support shaft 64, the hollow air chuck support shaft 74, and the reel support shaft 56 are all rotatably mounted in coaxial fashion along an axis of rotation, which is also the axis of rotation of the supply reel 36, the first air chuck 40, the second air chuck 42, and the take-up reel 38. Also, the reel drive pulley 52, the air chuck drive pulley 72, the air chuck drive pulley 82, and 62 are all of the same diameter. They will all be driven by a drive shaft 84, which is rotatably mounted at seven locations to bearing supports 86, 88, 90, 92, 94, 96, and 98.

A drive motor 100 having a drive pulley 102 mounted on its shaft drives a drive belt 104 that in turn drives a motor drive pulley 106 mounted on the drive shaft 84. Two drive pulleys 108 and 110 respectively drive two drive belts 112 and 114, which respectively drive the reel drive pulleys 52 and 62. Two drive pulleys 116 and 118 respectively drive two drive belts 120 and 122, which respectively drive the air chuck drive pulleys 72 and 82. The drive motor 100 may be a 3-phase AC motor, for example, which may be precisely operated so that the rotation of the continuous length of tubing 32 (which rotates with the supply reel 36, the first air chuck 40, the second air chuck 42, and the take-up reel 38) may be precisely controlled, which will be particularly important for the segment of the continuous length of tubing 32 located intermediate the first air chuck 40 and the second air chuck 42.

The apparatus 30 for winding wire-reinforcement segments includes a mechanism for driving the take-up reel 38 to wind up (or unwind) portions of the continuous length of tubing 32 upon which wire windings have been wound. A drive carriage 124 is mounted for movement in a direction parallel to the axis of rotation of the supply reel 36, the first air chuck 40, the second air chuck 42, and the take-up reel 38. The drive carriage 124 is supported on one side by a support rail 126 and on the other side by a threaded drive actuator 128, which is operated by a drive motor 130 which moves the drive carriage 124 toward and away from the take-up reel 38.

Mounted on the drive carriage 124 is a motor 132 driving a rod 134 upon which two frictional drive wheels 136 are mounted. The rod 134 is supported by two support bearings 138. When the drive carriage 124 is moved toward the take-up reel 38, the frictional drive wheels 136 come into frictional contact with the take-up reel 38, and the motor 132 drives the rod 134 and the frictional drive wheels 136 to rotate the take-up reel 38 to the extent required to wind up any slack portion of the continuous length of tubing 32 upon which wire windings have been wound.

Optionally, the apparatus 30 for winding wire-reinforcement segments may also include a mechanism for driving the supply reel 36 to advance (or rewind) portions of the continuous length of tubing 32 upon which wire windings have not yet been wound. A drive carriage 140 is mounted for movement in a direction parallel to the axis of rotation of the supply reel 36, the first air chuck 40, the second air chuck 42, and the take-up reel 38. The drive carriage 140 is supported on one side by a support rail 142 and on the other side by a threaded drive actuator 144, which is operated by a drive motor 146 which moves the drive carriage 140 toward and away from the supply reel 36.

Mounted on the drive carriage 140 is a motor 148 driving a rod 150 upon which two frictional drive wheels 152 are mounted. The rod 150 is supported by two support bearings 154. When the drive carriage 140 is moved toward the supply reel 36, the frictional drive wheels 152 come into frictional contact with the supply reel 36, and the motor 148 drives the rod 150 and the frictional drive wheels 152 to rotate the supply reel 36 to the extent required to supply or retract the continuous length of tubing 32.

Once a segment of the continuous length of tubing 32 is operatively secured between the first air chuck 40 and the second air chuck 42, a coil wire dereeler 156 is used to wind coil wire 158 onto selected portions of the segment of the continuous length of tubing 32. The coil wire dereeler 156 includes a dereeler carriage 160 supported for movement in an axial direction parallel to the axis of rotation of the supply reel 36, the first air chuck 40, the second air chuck 42, and the take-up reel 38 on a support rail 162 and by a threaded drive actuator 164.

The threaded drive actuator 164 is operated by a drive motor 166 which moves the dereeler carriage 160 in its axial direction in a highly precise manner. The drive motor 166 may be a 3-phase AC motor, for example, which may be precisely operated so that the position and the rate of movement of the dereeler carriage 160 on the support rail 162 may be precisely controlled, which will be particularly important for the spacing of windings of the coil wire 158 on the segment of the continuous length of tubing 32 located intermediate the first air chuck 40 and the second air chuck 42.

The coil wire 158 is supplied from a supply reel 168 located on the back end of the dereeler carriage 160, and the coil wire 158 from the supply reel 168 is fed through a tensioning mechanism 170 to a nozzle 172 positioned close adjacent the segment of the continuous length of tubing 32 located between the first air chuck 40 and the second air chuck 42, at which location the coil wire 158 is wound around the continuous length of tubing 32. The portion of the dereeler carriage 160 terminating in the tensioning mechanism 170 may be thought of as a "winding arm," since it is from this "winding arm" that the coil wire 158 will be wound onto the segment of the continuous length of tubing 32 located between the first air chuck 40 and the second air chuck 42. It will be appreciated by those skilled in the art that by simultaneously rotating the continuous length of tubing 32 located between the first air chuck 40 and the second air chuck 42 and moving the dereeler carriage 160 in its axial direction, a segment of the coil wire 158 may be wound onto the continuous length of tubing 32.

Figure 3:
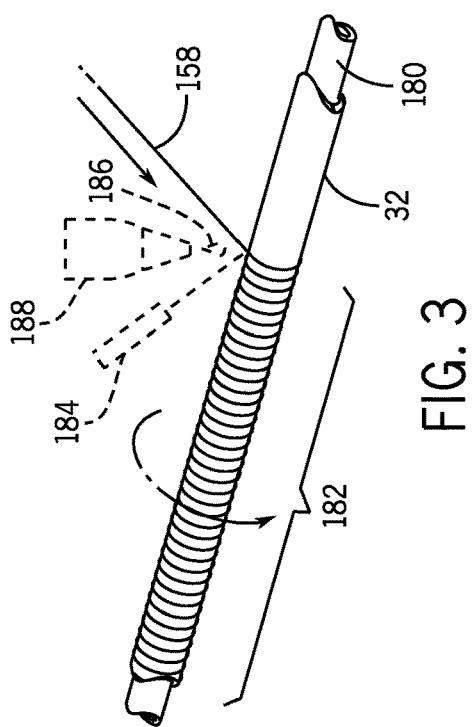
FIG. 3 is an isometric view of wire being helically wound onto the tubing as the tubing is rotated.

At this point, an optional aspect of the wire-reinforced tubing product and manufacturing method of the present invention will be introduced. Referring now to FIG. 3, the continuous length of tubing 32 optionally has a thicker walled segment of plastic support tubing 180 located inside the continuous length of tubing 32 to stiffen and support the thinner walled continuous length of tubing 32. It will be understood that the thicker walled segment of plastic support tubing 180 is used during the manufacturing process in order to both aid in the gripping of the continuous length of tubing 32 by the first air chuck 40 and the second air chuck 42, as well as to provide the continuous length of tubing 32 with additional firmness as the coil wire 158 is wound thereupon.

In order to initiate the winding of the coil wire 158 onto the continuous length of tubing 32, the coil wire 158 is wound around the segment of the continuous length of tubing 32 at a location adjacent to the second air chuck 42 by hand to start a loop. The coil wire 158 is then held in the second air chuck 42 which when clamped shut secures the coil wire 158 on the continuous length of tubing 32. This will allow the coil wire 158 to be wound around the extruded core when the reel support shaft 46, the hollow air chuck support shaft 64, the hollow air chuck support shaft 74, and the reel support shaft 56 are rotated. Almost all of the time the first segment or length of the coil wire 158 wound on the continuous length of tubing 32 is sacrificial and only there to get the machine "threaded."

Referring again to FIG. 3, when a segment 182 of the coil wire 158 has been wound onto the continuous length of tubing 32, the end of the segment 182 of the coil wire 158 must be secured to maintain the segment 182 of the coil wire 158 in position on the continuous length of tubing 32. This may be done in several different manners, including, for example, by using a weld to hold the last two windings of the segment 182 of the coil wire 158 together, or by using a high strength adhesive to hold the last two windings of the segment 182 of the coil wire 158 together. A weld may be placed using a laser 184 shown schematically, or a drop of high strength adhesive 186 may be placed from a source 188 of the high strength adhesive 186 also shown schematically.

It will also be appreciated that the first two windings in a segment 182 of the coil wire 158 may also be held together in the same manner.

Figure 4A:
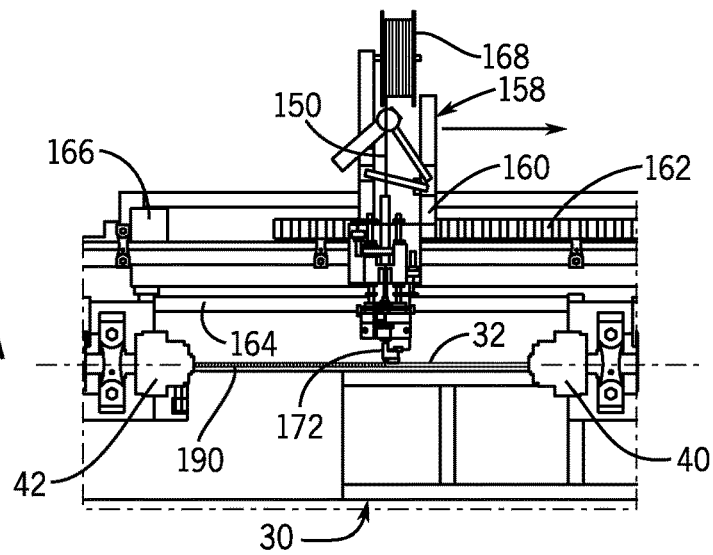
FIG. 4A is a partial top plan view of the apparatus shown in FIG. 1 showing a long first winding wound onto a segment of the tubing from a moving coil wire dereeler.
Figure 4B:
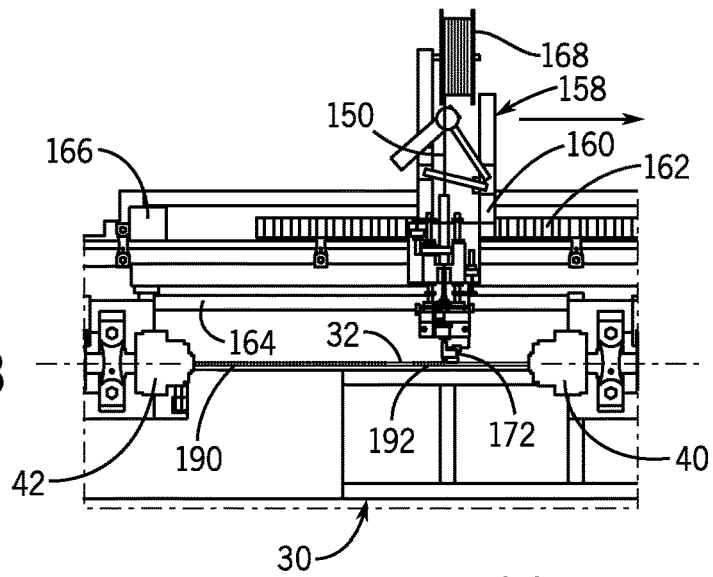
FIG. 4B is a partial top plan view of the apparatus shown in FIG. 1 showing a short second winding wound onto the segment of the tubing from a moving coil wire dereeler.
Figure 4C:
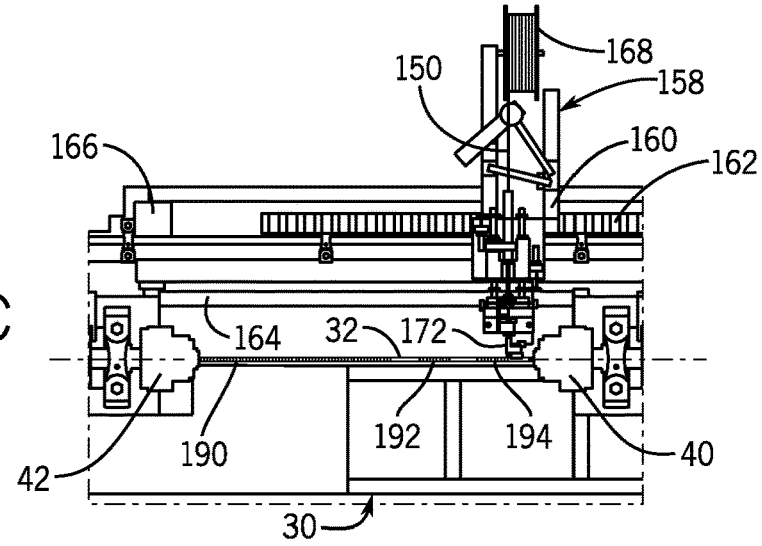
FIG. 4C is a partial top plan view of the apparatus shown in FIG. 1 showing a short third winding wound onto the segment of the tubing from a moving coil wire dereeler.

Referring next to FIGS. 4A, 4B, and 4C, the creation of three windings on the continuous length of tubing 32 between the first air chuck 40 and the second air chuck 42 is illustrated. A long first winding 190 is wound from a position close adjacent the second air chuck 42 to the position adjacent to the nozzle 172 of the coil wire dereeler 156 by rotating the supply reel 36, the first air chuck 40, the second air chuck 42, and the take-up reel 38 to thereby rotate the continuous length of tubing 32, while simultaneously moving the dereeler carriage 160 in its axial direction from left to right as shown in FIG. 4A.

After the long first winding 190 has been wound and its ends are both secured, the dereeler carriage 160 is moved in its axial direction from left to right a spaced distance between the end of the long first winding 190 and the beginning of the next winding without rotating the continuous length of tubing 32 between the first air chuck 40 and the second air chuck 42 by rotating the supply reel 36, the first air chuck 40, the second air chuck 42, and the take-up reel 38. A short second winding 192 is wound from this position to the position adjacent to the nozzle 172 of the coil wire dereeler 156 shown in FIG. 4B by rotating the supply reel 36, the first air chuck 40, the second air chuck 42, and the take-up reel 38 to thereby rotate the continuous length of tubing 32, while simultaneously moving the dereeler carriage 160 in its axial direction from left to right.

After the short second winding 192 has been wound and its ends are both secured, the dereeler carriage 160 is moved in its axial direction from left to right a spaced distance between the end of the short second winding 192 and the beginning of the next winding without rotating the continuous length of tubing 32 between the first air chuck 40 and the second air chuck 42 by rotating the supply reel 36, the first air chuck 40, the second air chuck 42, and the take-up reel 38. A short third winding 194 is wound from this position to the position adjacent to the nozzle 172 of the coil wire dereeler 156 shown in FIG. 4C by rotating the supply reel 36, the first air chuck 40, the second air chuck 42, and the take-up reel 38 to thereby rotate the continuous length of tubing 32, while simultaneously moving the dereeler carriage 160 in its axial direction from left to right.

Figure 5:
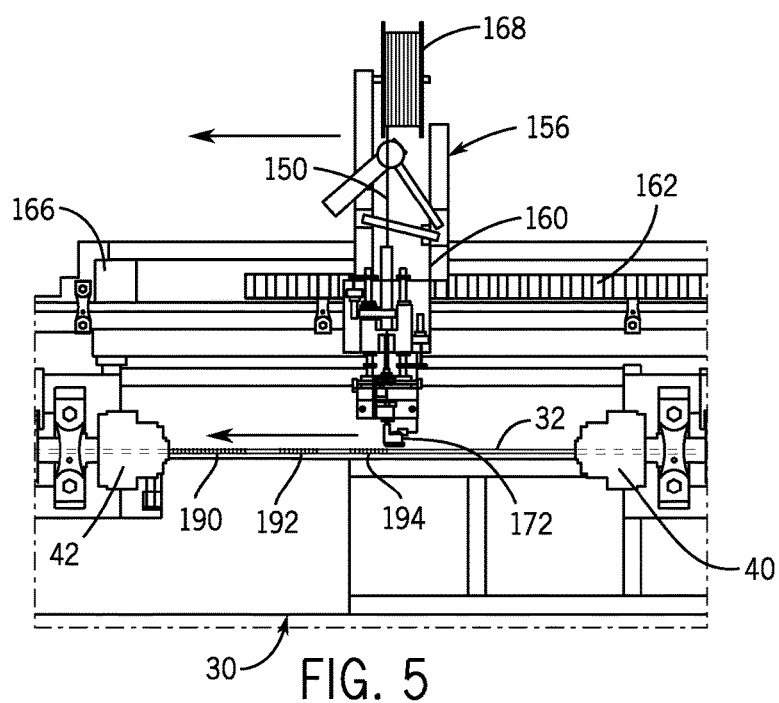
FIG. 5 is a partial top plan view of the apparatus shown in FIG. 1 showing the coil wire dereeler being used to move the segment of tubing with the three windings thereupon out of the winding area and to bring in a new segment of tubing onto which windings will subsequently be wound.

Moving next to FIG. 5, the manner in which the segment of the continuous length of tubing 32 between the first air chuck 40 and the second air chuck 42 on which the three windings 190, 192, and 194 have been wound is moved out of the winding area between the first air chuck 40 and the second air chuck 42 to bring in a new segment of the continuous length of tubing 32 onto which windings will subsequently be wound into place. This is done by releasing both of the first air chuck 40 and the second air chuck 42, and having the coil wire dereeler 156 grip the coil wire 158 and move to the left back to its position as shown in FIG. 1, thereby using the coil wire 158 to slide the segment of the continuous length of tubing 32 that was between the first air chuck 40 and the second air chuck 42 to thereby expose a new segment of the continuous length of tubing 32 between the first air chuck 40 and the second air chuck 42 upon which windings may be made. Simultaneously, the supply reel 36 will dispense a sufficient additional length of the continuous length of tubing 32, and the take-up reel 38 will be driven to wind up the advanced portion of the continuous length of tubing 32.

Figure 6:
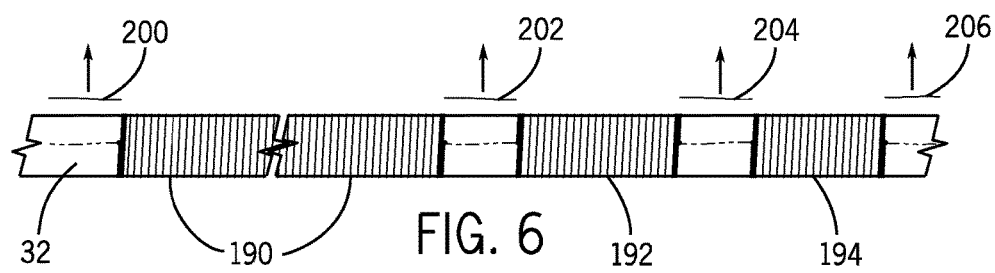
FIG. 6 is an isometric view of the segment of tubing with the three windings wound thereupon in FIGS. 4A-4C showing a schematic depiction of the segments of wire intermediate the windings being removed.

Turning now to FIG. 6, after windings 190, 192, and 194 have been wound on the entire length of the continuous length of tubing 32, it will be appreciated that all of the windings 190, 192, and 194 are connected together by straight lengths of the coil wire 158. In FIG. 6, the removal of four of these straight lengths 200, 202, 204, and 206 of the coil wire 158 is shown schematically, which removal may be performed in any suitable manner, either manual or automatic.

Now that the windings 190, 192, and 194 on the entire length of the continuous length of tubing 32 are complete, the outer surface of the continuous length of tubing 32 with multiple sets of windings 190, 192, and 194 thereupon must have a protective outer layer of material applied thereto. Moving first to FIG. 7, a sprayer 210 is shown applying a coating spray 212 to the outer surface of the continuous length of tubing 32 with multiple sets of windings 190, 192, and 194 thereupon, with an applied outer coating 214 being uniformly applied over the outer surface of the continuous length of tubing 32 and the multiple sets of windings 190, 192, and 194.

Figure 8:
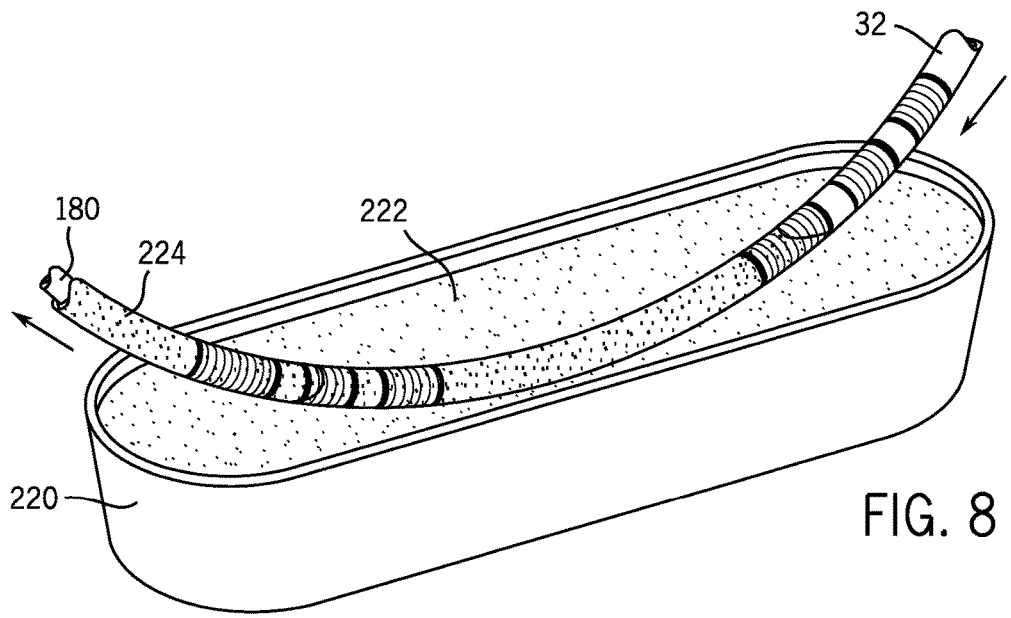
FIG. 8 is an isometric view of a coating being applied to the outer surface of the continuous length of tubing with multiple sets of windings thereupon by dipping the continuous length of tubing with multiple sets of windings thereupon into a container of coating solution to coat the outer surface.

Turning next to FIG. 8, the outer surface of the continuous length of tubing 32 with multiple sets of windings 190, 192, and 194 thereupon is passed through a container 220 having a coating material 222 therein, which results in an applied outer coating 224 being uniformly applied over the outer surface of the continuous length of tubing 32 and the multiple sets of windings 190, 192, and 194.

Figure 9:
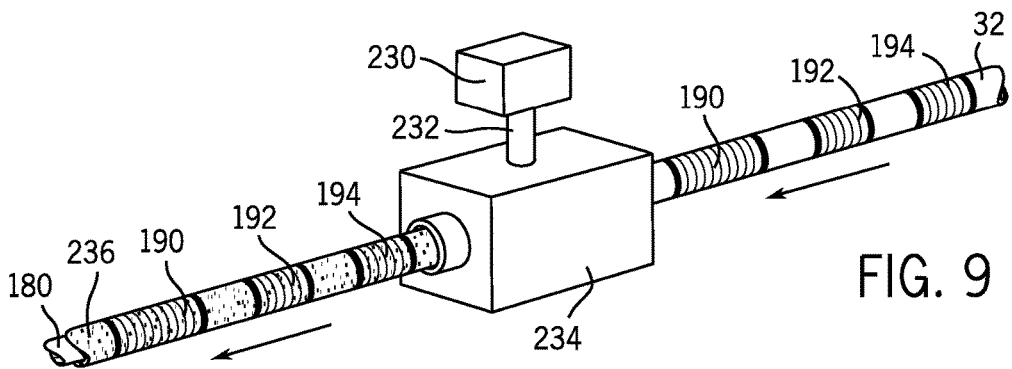
FIG. 9 is an isometric view of a coating being applied to the outer surface of the continuous length of tubing with multiple sets of windings thereupon by extruding the coating onto the outer surface.

Turning now to FIG. 9, coating solution provided by a coating solution supply 230 is supplied through a supply tube 232 to an extruder 234. The continuous length of tubing 32 with multiple sets of windings 190, 192, and 194 thereupon is fed through the extruder 234, with the extruder 234 extruding an applied outer coating 236 onto the outer surface of the continuous length of tubing 32 and the multiple sets of windings 190, 192, and 194.

Moving next to FIG. 10, a segment of the continuous length of tubing 32 on which the windings 190, 192, and 194 are located which also contains the optional thicker walled segment of plastic support tubing 180 therein is shown having the thicker walled segment of plastic support tubing 180 removed therefrom. This may be done by mechanically pulling on one end of the thicker walled segment of plastic support tubing 180, which will reduce its outer diameter, thereby aiding its removal from the continuous length of tubing 32.

Next, in FIG. 11, a single wire-reinforced tubing segment 240 which has been cut from the continuous length of tubing 32 on which multiple sets of the windings 190, 192, and 194 are located. It will be appreciated that the configuration of the wire-reinforced tubing segment 240 shown in FIG. 8, with the long first winding 190, the short second winding 192, and the short third winding 194, is but one example of the many different configurations of wire-reinforced tubing segment which can be made through the use of the present invention.

Figure 12:
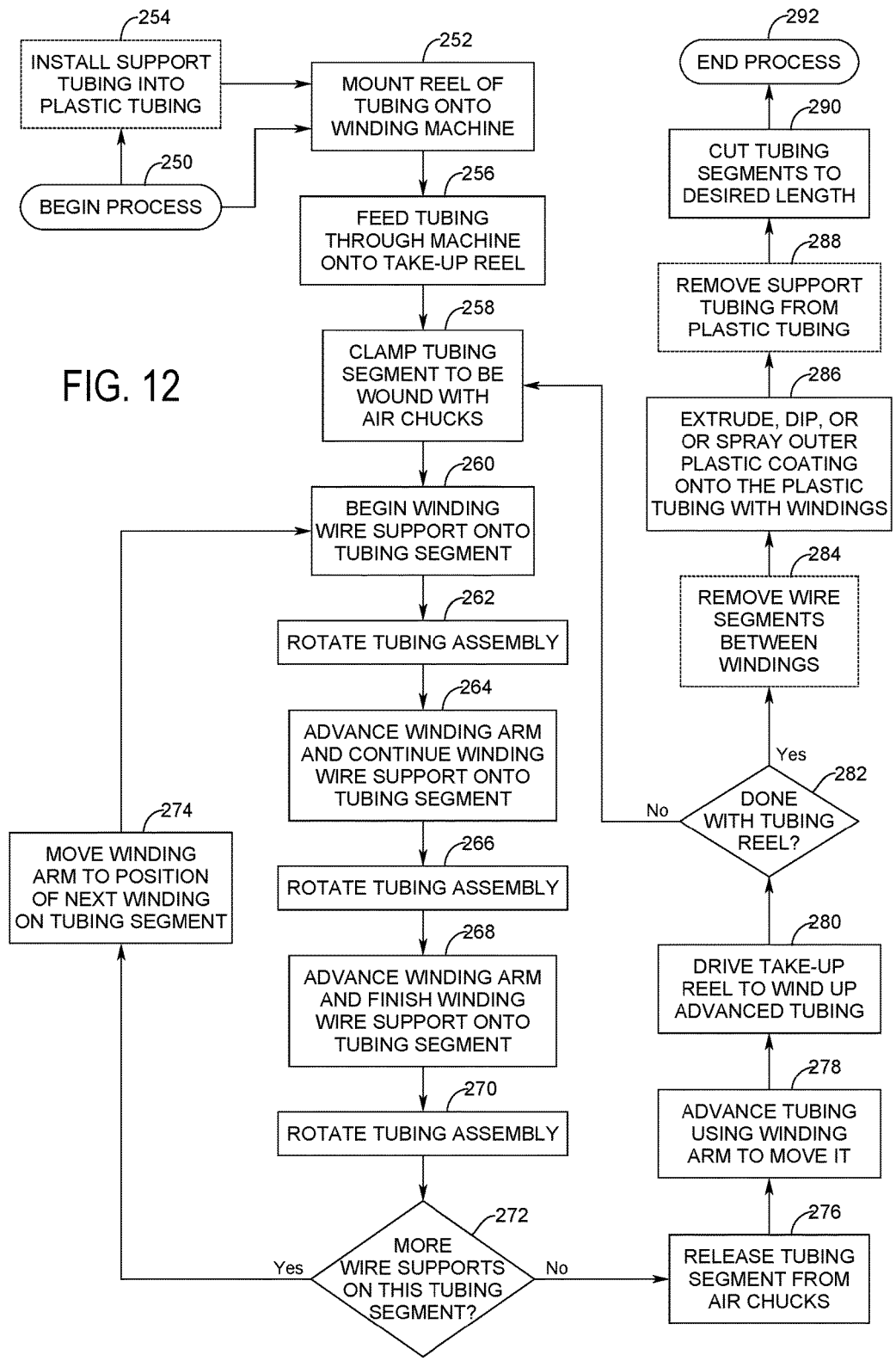
FIG. 12 is a flowchart illustrating an embodiment of a method for manufacturing the wire-reinforced tubing product shown in FIGS. 1-11.

Turning finally to FIG. 12, a method for manufacturing the wire-reinforced tubing product and manufacturing method of the present invention is illustrated and may be discussed in conjunction with the FIGS. 1-11, as applicable. The method begins in a process initiation step 250, and moves first to a mount reel of tubing onto winding machine step 252 in which the supply reel 36 of the continuous length of tubing 32 is mounted onto the apparatus 30 for winding wire-reinforcement segments (all shown in FIG. 1). In an optional aspect of the present invention, if it is desired to use the thicker walled segment of plastic support tubing 180 (shown in FIG. 3) inside the continuous length of tubing 32, the thicker walled segment of plastic support tubing 180 is installed in the continuous length of tubing 32 in an install support tubing into plastic tubing step 254 prior to the mount reel of tubing onto winding machine step 252.

From the mount reel of tubing onto winding machine step 252, the process moves to a feed tubing onto take-up reel step 256, where the continuous length of tubing 32 is fed consecutively through the hollow guide cone 70, the hollow air chuck support shaft 64, the first air chuck 40, the second air chuck 42, the hollow air chuck support shaft 74, and the hollow guide cone 80, and onto the take-up reel 38. Next, in a clamp tubing segment between air chucks step 258, a segment of the continuous length of tubing 32 is clamped in the air chuck drive pulley 72 and the hollow air chuck support shaft 74.

The coil wire 158 is started to be wound onto the continuous length of tubing 32 in a begin winding wire onto tubing step 260, with the continuous length of tubing 32 initially being rotated in a rotate tubing segment step 262 to begin a winding (such as the long first winding 190), with the beginning of the winding being secured by a weld or adhesive as described previously. Next, in an advance winding arm to wind winding onto tubing step 264, the dereeler carriage 160 is advanced as the continuous length of tubing 32 continues to be rotated in the rotate tubing segment step 266. The process continues in an advance winding arm to finish winding onto tubing step 268 with the continuous length of tubing 32 being rotated in a rotate tubing segment 270 to finish the winding, with the end of the winding being secured by a weld or adhesive as described previously.

The method then moves to a more winding determination step 272 in which it is determined whether or not there is to be another winding in the segment of the continuous length of tubing 32 between the first air chuck 40 and the second air chuck 42. If there is to be another winding in this segment of the continuous length of tubing 32, the process moves to a move winding arm to wind next winding tubing step 274 in which the dereeler carriage 160 is advanced to bring the winding arm to the location at which another winding is to begin. The process then moves from the move winding arm to wind next winding tubing step 274 back to the begin winding wire onto tubing step 260.

If, on the other hand, it is determined in the more winding determination step 272 that no additional winding is to be made in the segment of the continuous length of tubing 32 between the first air chuck 40 and the second air chuck 42, the process moves to a release tubing segment from air chucks step 276 in which the segment of the continuous length of tubing 32 that has been clamped between the air chuck drive pulley 72 and the hollow air chuck support shaft 74 is released by unclamping the first air chuck 40 and the second air chuck 42. Next, in an advance tubing using winding arm step 278, the end of the last winding that has been wound is moved by moving the dereeler carriage 160, while simultaneously operating the take-up reel 38 in a drive take-up reel to wind up advanced tubing step 280 to advance the continuous length of tubing 32 to bring a new segment of tubing into position between the first air chuck 40 and the second air chuck 42.

Next, in a done with tubing reel determination step 282, it is determined whether more sets of windings are to be made on the supply reel 36 of the continuous length of tubing 32. If more sets of windings are to be made, the method moves back to the clamp tubing segment between air chucks step 258 to make such additional windings. If, on the other hand, no more sets of windings are to be made on the supply reel 36 of the continuous length of tubing 32, the method moves instead to a remove wire segments between windings step 284 where the wire segments such as the straight length 202 of the coil wire 158, the straight length 204 of the coil wire 158, the straight length 206 of the coil wire 158, and 208 are removed from between the long first winding 190, the short second winding 192, and the short third winding 194 (all shown in FIG. 6).

Figure 7:
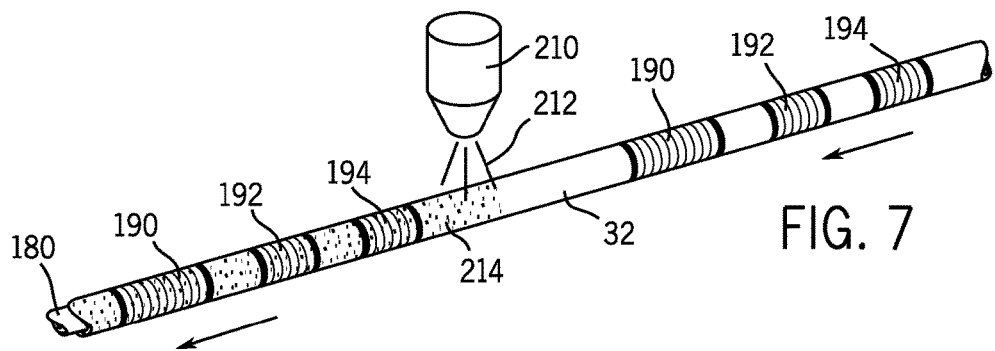
FIG. 7 is an isometric view of a coating being applied to the outer surface of the continuous length of tubing with multiple sets of windings thereupon by spraying the coating from a sprayer onto the outer surface.

The method then moves to a extrude, dip, or spray plastic coating onto tubing with windings step 286 in which the protective outer layer of material is applied to the outer surface of the continuous length of tubing 32 with multiple sets of windings 190, 192, and 194 thereupon (as shown in FIG. 7, 8, or 9). Next, the method moves to an optional remove support tubing from plastic tubing step 288 in which the thicker walled segment of plastic support tubing 180, if it was used, is removed from the continuous length of tubing 32 with the multiple sets of windings 190, 192, and 194 thereupon (as shown in FIG. 10).

The method next moves to a cut tubing segments to desired length step 290 in which the continuous length of tubing 32 with the multiple sets of windings 190, 192, and 194 thereupon is cut into discrete wire-reinforced tubing segments 240 (shown in FIG. 11). Finally, the method concludes in a process termination step 292.

It may therefore be appreciated from the above detailed description of the preferred embodiment of the present invention that it provides an apparatus that may be used to produce an improved wire-reinforced tubing product. The wire-reinforced tubing product produced by the apparatus and method of the present invention is advantageous for use with medical and other applications. Finally, the wire-reinforced tubing apparatus and method of the present invention achieves numerous advantages without incurring any substantial relative disadvantage.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A method of manufacturing wire-reinforced plastic tubing segments, comprising:
   supplying an extended length segment of plastic tubing from a supply reel;
   supporting a portion of the plastic tubing supplied from the supply reel intermediate two spaced-apart air chucks, the portion of the plastic tubing located intermediate the air chucks defining an axis of rotation;
   taking up the plastic tubing onto a take-up reel;
   simultaneously rotating the supply reel, the air chucks, and the take-up reel about the axis of rotation while supplying a reinforcing wire to the portion of the plastic tubing located intermediate the air chucks to helically wind at least one wire winding onto the portion of the plastic tubing located intermediate the air chucks;
   releasing the air chucks and advancing the plastic tubing from the supply reel to the take-up reel to advance a subsequent portion of the plastic tubing to the location between the air chucks and supporting the subsequent portion of the plastic tubing with the air chucks;
   repeating the rotating and releasing steps;
   installing an outer plastic layer over the exterior of the plastic tubing and the wire windings thereupon; and
   cutting the plastic tubing into segments each having at least one wire winding.

2. A method as defined in claim 1, wherein the extended length segment of plastic tubing is made of a thermoplastic elastomer such as polyurethane.

3. A method as defined in claim 1, additionally comprising:
   inserting a segment of plastic support tubing inside the extended length segment of plastic tubing prior to the supplying step; and
   removing the segment of plastic support tubing from the extended length segment of plastic tubing prior to the cutting step.

4. A method as defined in claim 3, wherein the plastic support tubing is stiffer than the extended length segment of plastic tubing.

5. A method as defined in claim 4, wherein the plastic support tubing has a thicker wall thickness than the extended length segment of plastic tubing.

6. A method as defined in claim 1, additionally comprising:
   securing first and second opposite ends of the at least one wire winding onto the portion of the plastic tubing located intermediate the air chucks.

7. A method as defined in claim 6, wherein the securing step is performed by welding the first and second opposite ends of the at least one wire winding.

8. A method as defined in claim 6, wherein the securing step is performed by adhesively securing the first and second opposite ends of the at least one wire winding.

9. A method as defined in claim 1, wherein the rotating step is performed to helically wind at least two spaced-apart wire windings onto the portion of the plastic tubing located intermediate the air chucks.

10. A method as defined in claim 1, wherein the installing step comprises:
    spraying a plastic coating onto the extended length segment of plastic tubing with multiple sets of wire windings thereupon.

11. A method as defined in claim 1, wherein the installing step comprises:
    passing the extended length segment of plastic tubing with multiple sets of wire windings thereupon through a container having a coating material therein to apply an outer coating onto the extended length segment of plastic tubing with multiple sets of wire windings thereupon.

12. A method as defined in claim 1, wherein the installing step comprises:
    feeding the extended length segment of plastic tubing with multiple sets of wire windings thereupon through an extruder to extrude an outer coating onto the extended length segment of plastic tubing with multiple sets of wire windings thereupon.

13. A method of manufacturing wire-reinforced plastic tubing segments, comprising:
    supplying an extended length segment of plastic tubing having an extended length segment of plastic support tubing located inside the extended length segment of plastic tubing from a supply reel;
    supporting a portion of the plastic tubing/plastic support tubing supplied from the supply reel intermediate two spaced-apart air chucks, the portion of the plastic tubing/plastic support tubing located intermediate the air chucks defining an axis of rotation;
    taking up the plastic tubing/plastic support tubing onto a take-up reel;
    simultaneously rotating the supply reel, the air chucks, and the take-up reel about the axis of rotation while supplying a reinforcing wire to the portion of the plastic tubing/plastic support tubing located intermediate the air chucks to helically wind at least one wire winding onto the portion of the plastic tubing/plastic support tubing located intermediate the air chucks;
    welding first and second opposite ends of the at least one wire winding that is helically wound onto the portion of the plastic tubing/plastic support tubing located intermediate the air chucks;
    releasing the air chucks and advancing the plastic tubing/plastic support tubing from the supply reel to the take-up reel to advance a subsequent portion of the plastic tubing/plastic support tubing to the location between the air chucks and supporting the subsequent portion of the plastic tubing/plastic support tubing with the air chucks;
    repeating the rotating, welding, and releasing steps;
    installing an outer plastic layer over the exterior of the plastic tubing and the wire windings thereupon;
    cutting the plastic tubing into segments each having at least one wire winding; and
    removing the plastic support tubing from the segments of plastic tubing.

14. A method of manufacturing wire-reinforced plastic tubing segments, comprising:
    providing an extended length segment of plastic tubing;
    supporting a portion of the plastic tubing intermediate two spaced-apart air chucks, the portion of the plastic tubing located intermediate the air chucks defining an axis of rotation;
    simultaneously rotating the air chucks about the axis of rotation while helically winding a wire winding onto the portion of the plastic tubing located intermediate the air chucks;
    releasing the air chucks and advancing the plastic tubing to provide a subsequent portion of the plastic tubing to the location between the air chucks and supporting the subsequent portion of the plastic tubing with the air chucks;
    repeating the rotating and releasing steps;

installing an outer plastic layer over the exterior of the plastic tubing and the wire windings thereupon; and cutting the plastic tubing into segments each having at least one wire winding.

15. A method as defined in claim 14, additionally comprising:

inserting a segment of plastic support tubing inside the extended length segment of plastic tubing prior to the providing step; and removing the segment of plastic support tubing from the extended length segment of plastic tubing prior to the cutting step.

16. An apparatus for manufacturing wire-reinforced plastic tubing segments, comprising:

a supply reel at one end of the apparatus that is arranged and configured to contain a supply of an extended length segment of plastic tubing;

a take-up reel at an opposite end of the apparatus that is arranged and configured to take up the plastic tubing;

two spaced-apart air chucks located on the apparatus intermediate the supply reel and the take-up reel, the air chucks supporting a portion of the plastic tubing supplied from the supply reel that is located intermediate the air chucks and that defines an axis of rotation; and a mechanism configured to supply a reinforcing wire to the portion of the plastic tubing located intermediate the air chucks while the supply reel, the air chucks, and the take-up reel are simultaneously rotated about the axis of rotation to helically wind at least one wire winding onto the portion of the plastic tubing located intermediate the air chucks; wherein the apparatus is arranged and configured to release the air chucks and advance the plastic tubing from the supply reel to the take-up reel to advance a subsequent portion of the plastic tubing to the location between the air chucks and support the subsequent portion of the plastic tubing with the air chucks, following which the rotating and releasing steps are repeated to helically wind additional wire windings onto the portion of the plastic tubing located intermediate the air chucks.

17. An apparatus as defined in claim 16, additionally comprising:

apparatus for installing an outer plastic layer over the exterior of the plastic tubing and the portions of the reinforcing wire helically wound thereupon.

18. An apparatus as defined in claim 16, additionally comprising:

apparatus for cutting the plastic tubing into segments each having at least one wire winding thereupon.

19. An apparatus as defined in claim 16, additionally comprising:

apparatus for inserting a segment of plastic support tubing inside the extended length segment of plastic tubing prior to the supplying step; and apparatus for removing the segment of plastic support tubing from the extended length segment of plastic tubing prior to the cutting step.

20. An apparatus as defined in claim 16, wherein the mechanism supplying a reinforcing wire to the portion of the plastic tubing located intermediate the air chucks is configured to helically wind at least two wire windings onto the portion of the plastic tubing located intermediate the air chucks supply while the supply reel, the air chucks, and the take-up reel are simultaneously rotated about the axis of rotation.

* * * * *